(12) United States Patent
Warner et al.

(10) Patent No.: US 6,858,148 B2
(45) Date of Patent: Feb. 22, 2005

(54) METHOD AND APPARATUS FOR DETECTING CHEMICAL BINDING

(75) Inventors: Benjamin P. Warner, Los Alamos, NM (US); George J. Havrilla, Los Alamos, NM (US); Thomasin C. Miller, Los Alamos, NM (US); Cyndi A. Wells, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 49 days.

(21) Appl. No.: 10/621,825

(22) Filed: Jul. 16, 2003

(65) Prior Publication Data

US 2005/0011818 A1 Jan. 20, 2005

(51) Int. Cl.[7] .............................................. B01D 15/08
(52) U.S. Cl. ...................... 210/656; 210/198.2; 436/56; 436/58; 435/7.1; 378/46
(58) Field of Search ................................. 210/656, 659, 210/198.2; 378/44, 45, 46, 47, 48, 49, 57; 436/56, 58, 57; 435/5, 6, 7.1

(56) References Cited

U.S. PATENT DOCUMENTS

| | | | | |
|---|---|---|---|---|
| 4,832,881 A | * | 5/1989 | Arnold et al. ............. 264/29.7 |
| 5,482,867 A | * | 1/1996 | Barrett et al. ............... 436/518 |
| 5,506,107 A | * | 4/1996 | Cunningham et al. ..... 435/7.21 |
| 5,641,640 A | | 6/1997 | Hanning .................... 435/7.92 |
| 5,965,456 A | | 10/1999 | Malmqvist et al. ......... 436/514 |
| 6,147,344 A | | 11/2000 | Annis et al. ................ 250/281 |
| 6,225,132 B1 | * | 5/2001 | Drukier et al. ............. 436/541 |
| 6,344,334 B1 | | 2/2002 | Ellman et al. ............... 435/7.1 |
| 6,395,169 B1 | | 5/2002 | Hindsgaul et al. ....... 210/198.2 |
| 6,496,562 B1 | * | 12/2002 | Henrich et al. ............... 378/90 |
| 2003/0020254 A1 | * | 1/2003 | Weaver, II ................. 280/252 |
| 2003/0027129 A1 | | 2/2003 | Warner .......................... 435/5 |

OTHER PUBLICATIONS

George J. Havrilla et al., "Flow Method and Apparatus for Screening Chemicals Using Micro X–Ray Fluorescence," U.S. Appl. No. 10/206,524, filed Jul. 25, 2002.

Bruce Alberts, Dennis Bray, Julian Lewis, Martin Raff, Keith Roberts, and James D. Watson, "Molecular Biology of the Cell," Second Edition, pp. 159–160, 1989.

(List continued on next page.)

Primary Examiner—Ernest G. Therkorn
(74) Attorney, Agent, or Firm—Samuel L. Borkowsky

(57) ABSTRACT

The method for screening binding between a target binder and potential pharmaceutical chemicals involves sending a solution (preferably an aqueous solution) of the target binder through a conduit to a size exclusion filter, the target binder being too large to pass through the size exclusion filter, and then sending a solution of one or more potential pharmaceutical chemicals (preferably an aqueous solution) through the same conduit to the size exclusion filter after target binder has collected on the filter. The potential pharmaceutical chemicals are small enough to pass through the filter. Afterwards, x-rays are sent from an x-ray source to the size exclusion filter, and if the potential pharmaceutical chemicals form a complex with the target binder, the complex produces an x-ray fluorescence signal having an intensity that indicates that a complex has formed.

7 Claims, 3 Drawing Sheets

OTHER PUBLICATIONS

M. C. Ringo, M. S. Huhta, G. Shea–McCarthy, J. E. Penner–Hahn, and C. E. Evans, "On–Line X–ray Fluorescence Detection for Capillary Electrophoresis Separations," Nuclear Instruments and Methods in Physics Research B, vol. 149, pp. 177–181, 1999.

Stephanie E. Mann, Moira C. Ringo, Grace Shea–McCarthy, James Penner–Hahn, and Christine E. Evans, "Element–Specific Detection in Capillary Electrophoresis Using X–ray Fluorescence Spectroscopy," Anal. Chem, vol. 72, No. 8, pp. 1754–1758, 2000.

C. Vogt, J. Vogt and H. Wittrisch, "Element–Sensitive X–ray Detection for Capillary Electrophoresis," Journal of Chromatography A, vol. 727, pp. 301–310, 1996.

Thomasin C. Miller, Martha R. Joseph, George J. Havrilla, Cris Lewis, and Vahid Majid, "Capillary Electrophoresis Micro X–ray Fluorescence: A Tool for Benchtop Elemental Analysis," Analytical Chemistry, vol. 75, pp. 2048–2053, 2003.

* cited by examiner

METHOD AND APPARATUS FOR DETECTING CHEMICAL BINDING

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to a flow method for detecting chemical binding and characterizing the binding between a chemical and a target binder using x-ray fluorescence spectroscopy.

BACKGROUND OF THE INVENTION

The binding properties of a protein largely depend on the exposed surface amino acid residues of its polypeptide chain (see, for example, Bruce Alberts et al., "Molecular Biology of the Cell", $2^{nd}$ edition, Garland Publishing, Inc., New York, 1989; and H. Lodish et al., "Molecular Cell Biology", $4^{th}$ edition, W. H. Freeman and Company, 2000). These amino acid residues can form weak noncovalent bonds with ions and molecules. Effective binding generally requires the formation of many weak bonds at a "binding site," which is usually a cavity in the protein formed by a specific arrangement of amino acids. There must be a precise fit with the binding site for effective binding to occur.

Pharmaceutical chemicals are the active ingredients in drugs, and it is believed that their therapeutic properties are linked to their ability to bind to one or more binding sites. The shapes of these binding sites may differ greatly among different proteins, and even among different conformations of the same protein. Even slightly different conformations of the same protein may differ greatly in their binding abilities. For these reasons, it is extremely difficult to predict which chemicals will bind effectively to proteins. Research and development for a new pharmaceutical chemical for a drug, i.e. drug development, generally involves determining the binding affinities between a potential pharmaceutical chemical (preferably a water soluble organic chemical that can dissolve into the blood stream) and a target binder (generally a biological material such as an enzyme or non-enzyme protein, DNA, RNA, human cell, plant cell, animal cell, and the like) at many stages of the drug development process. The target binder may also be a microorganism (e.g. prion, virus, bacterium, spores, and the like) in whole or in part. The drug development process typically involves procedures for combining potential pharmaceutical chemicals with target binders, detecting chemical binding between the potential pharmaceutical chemicals and the target binders and determining the binding affinity and kinetics of binding of a target binder to a chemical to form a complex or the kinetics of release of a bound chemical from a complex. The binding affinity is defined herein as the associative equilibrium constant Ka, where Ka is defined by equation (1) below.

$$Ka = \frac{[\text{complex}]}{[\text{target binder}][\text{potential pharmaceutical chemical}]} \quad (1)$$

In equation (1), [complex] is the concentration in moles per liter of the target binder/potential pharmaceutical complex, [target binder] is the concentration in moles per liter of the target binder, and [potential pharmaceutical chemical] is the concentration in moles per liter of the potential pharmaceutical chemical. Nowadays, the drug development process may involve the rapid screening of hundreds or thousands of potential pharmaceutical chemicals in order to identify a "lead compound," which is one of the many tested that binds very strongly, i.e. has a high binding affinity, with a particular target binder. After such a lead compound has been identified, then other potential pharmaceutical chemicals similar in structure to the lead compound are synthesized and tested in order to determine which of these potential pharmaceutical chemicals, if any, exhibits an even higher binding affinity. Some screening methods are described in the following patents, all of which are hereby incorporated by reference.

U.S. Pat. No. 6,147,344 to D. Allen Annis et al. entitled "Method for Identifying Compounds in a Chemical Mixture", which issued Nov. 14, 2000, describes a method for automatically analyzing mass spectrographic data from mixtures of chemical compounds.

U.S. Pat. No. 6,344,334 to Jonathan A. Ellman et al. entitled "Pharmacophore Recombination for the Identification of Small Molecule Drug Lead Compounds," which issued Feb. 5, 2002, describes a method for identifying a drug lead compound by contacting target biological molecules with cross-linked binding fragments.

U.S. Pat. No. 6,395,169 to Ole Hindsgaul et al. entitled "Apparatus for Screening Compound Libraries," which issued May 28, 2002, describes an apparatus that employs frontal chromatography combined with mass spectrometry to identify and rank members of a library that bind to a target receptor.

Some screening methods (fluorescence activated cell sorting, for example) cannot detect binding between many types of potential pharmaceutical chemicals (a non fluorescent antibody, for example) and a target binder unless the potential pharmaceutical chemical is provided with a chemical tag. Tagging may involve modifying the original chemical by attaching a "tag" (a chemical group that fluoresces when exposed to ultraviolet or visible light, for example) to a portion of the potential pharmaceutical chemical. Afterwards, the tagged chemicals are exposed to cells (muscle cells, for example) for a long enough period of time for binding to occur (if it does occur) to some of the cells to produce a cell/antibody complex. Afterwards, the cells are sent through a laser beam one at a time. The laser producing the beam is interfaced to a detector, such as an ultraviolet/visible fluorescence detector. The cell/antibody complexes produce a detectable fluorescence signal when exposed to the laser beam, and as the screening method proceeds, when a fluorescence signal is detected, the bound complexes that produce the signal are collected (see, for example, Bruce Alberts et al., "Molecular Biology of the Cell", $2^{nd}$ edition, Garland Publishing, Inc., New York, 1989, pages 159–160).

Another form of tagging involves attachment of the target binder to a surface. This type of tagging is used with surface plasmon resonance techniques (see, for example, U.S. Pat. No. 5,641,640 to A. Hanning entitled "Method of Assaying for an Analyte Using Surface Plasmon Resonance," which issued Jun. 24, 1997; and U.S. Pat. No. 5,595,456 to M. Malmqvist et al entitled "Analyte Detection," which issued Oct. 12, 1999, both hereby incorporated by reference).

It is generally assumed that the attachment of a fluorescent tag only serves to make visible to the instrument the otherwise invisible chemical and/or target binder, and that binding properties of the tagged and untagged materials are exactly the same. These assumptions may not be valid, as it is well known that even small changes to the structure of a chemical or target binder may affect its is function. Tagged materials are structurally different from their untagged counterparts, and these structural differences could affect their binding properties.

An efficient method for screening chemicals (with potential pharmaceutical activity, for example) for binding to target binders remains highly desirable.

Therefore, an object of the present invention is to provide an efficient method for screening chemicals for binding to target binders.

Another object of the present invention is to provide a screening method that does not require modification of a potential pharmaceutical chemical with a chemical tag.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the objects and purposes of the present invention, as embodied and broadly described herein, the present invention includes a screening method that involves sending a fluid that includes target binder through a conduit to a size exclusion filter, the target binder being too large to pass through the size exclusion filter; sending a second fluid that includes one or more chemicals through the conduit, the one or more chemicals capable of potentially binding to the target binder, the one or more chemicals being small enough to pass through the filter; sending x-rays into the conduit near the size exclusion filter; and monitoring any x-ray fluorescence signal produced from inside the conduit near the size exclusion filter.

The invention also includes an apparatus for screening binding between a target binder and a chemical. The apparatus includes an x-ray translucent conduit for fluid having target binder and chemical. A filter inside the conduit substantially blocks the flow of the target binder through the conduit but not the flow of the chemical. The apparatus also includes an x-ray excitation source capable of sending an x-ray beam through a volume of fluid inside the conduit, and an x-ray detector capable of receiving an x-ray fluorescence signal produced from the volume of fluid inside said conduit exposed to the x-ray beam.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings.

DETAILED DESCRIPTION OF THE INVENTION

Figure 1:
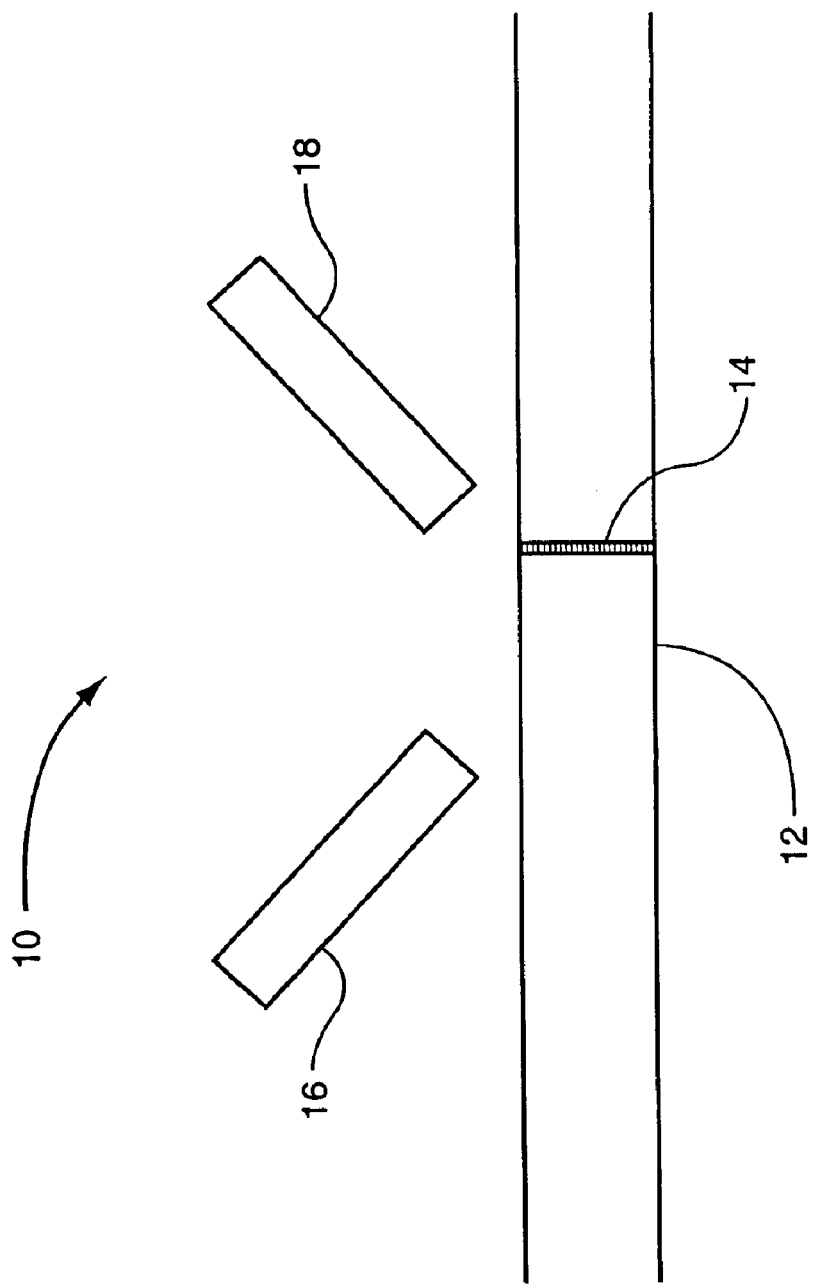
FIG. 1 shows a schematic representation of the apparatus of the invention.

The present invention includes a method for detecting and measuring binding affinities between chemicals and target binders. The method involves sending a solution (preferably an aqueous solution) of target binder through a conduit to a size exclusion filter. The target binders used with the invention are too large to pass through the size exclusion filter. After sending the target binder into the conduit, the amount of target binder near the size exclusion filter, upstream of the size exclusion filter, and downstream of the size exclusion filter may be quantified by sending x-rays to these sections and detecting any x-ray fluorescence signal due to the target binder. If an x-ray fluorescence signal due to the target binder is detected downstream of the particular filter used, then the filter may be damaged or the pore size may not be small enough to block the flow of target binder. After target binder collects on the size exclusion filter, a solution (preferably an aqueous solution) of one or more potential pharmaceutical chemicals is sent through the same conduit. The potential pharmaceutical chemicals used with the invention should be small enough to pass through the filter. The amount of the chemical(s) near the size exclusion filter, upstream of the size exclusion filter, and downstream of the size exclusion filter may be similarly quantified by x-ray fluorescence. Binding between target binder and a chemical to form a complex can occur anywhere along the conduit where target binder and chemical are present, most likely near the size exclusion filter where target binder collects.

The invention also includes an apparatus for detecting and measuring binding affinities between potential pharmaceutical chemicals and target binders. The apparatus includes a conduit and a size exclusion filter inside the conduit that is selected for passing the potential pharmaceutical chemical(s) but not the target binder(s). The apparatus also includes an x-ray source and an x-ray fluorescence detector.

The apparatus may include a collector for collecting materials that exit the conduit. Reservoirs may also be provided for the solutions of target binder, potential pharmaceutical chemicals, and for solvents and other types of solutions such as buffer solutions and solutions of denaturing and/or decomplexing agents.

Solutions of decomplexing agents can be used with the invention. A solution of decomplexing agent, for example, can be released into the conduit to promote the separation of a complex into its components of target binder and unbound chemical. After the chemical is released, another solution of potential pharmaceutical chemical (the chemical at a different concentration, a different chemical, etc.) can be introduced into the conduit and screened for binding to the same target binder.

Preferably, the apparatus is under the control of a programmable computer using software that can be used to control the apparatus by controlling the flow of target binder solution into the conduit, controlling the flow of solution of one or more selected potential pharmaceutical chemicals into the conduit, controlling the x-ray source (adjusting the position of the beam, the strength of the beam, etc.) receiving information related to any fluorescence signals received by the x-ray detector. The flow of any other solvents or solutions can also be under computer control.

The invention uses x-ray fluorescence to measure the binding affinity of a complex. The x-ray fluorescence is an important aspect of the invention because each chemical element has its own unique x-ray fluorescence spectrum and the intensity of the fluorescence is related to the concentration of that element in a chemical sample. Briefly, when an atom of a particular element is irradiated with x-ray radiation, the atom ejects a core electron such as a K shell electron. The resulting atom is in an excited state, and it can return to the ground state by replacing the ejected electron with an electron from a higher energy orbital. This is accompanied by the emission of an x-ray photon, i.e. x-ray fluorescence, and the photon energy is equal to the difference in the energies of the two electrons. Each element has a characteristic set of orbital energies and therefore, a characteristic x-ray fluorescence spectrum.

The use of x-ray fluorescence to detect binding events between target binders and receptors has been described in U.S. Patent Application 20030027129 to Benjamin P. Warner et al., entitled "Method for Detecting Binding Events Using Micro-X-ray Fluorescence Spectrometry," which was published Feb. 6, 2003, and in U.S. patent application Ser. No. 10/206,524 to George J. Havrilla et al. entitled "Flow Method and Apparatus for Screening Chemicals Using Micro-X-Ray Fluorescence," both hereby incorporated by reference. The use of capillary electrophoresis with x-ray fluorescence has been described by T. C. Miller et al. in "Capillary Electrophoresis Micro X-ray Fluorescence: A Tool for Benchtop Elemental Analysis," Analytical Chemistry, vol. 75, pp. 2048–2053, (2003); and by M. C. Ringo et al. in "On-line X-ray Fluorescence Detection for Capillary Electrophoresis Separations," Nuclear Instruments and Methods in Physics Research B, vol. 149, pp. 177–181, 1999; and by S. E. Mann et al. in "Element-Specific Detection in Capillary Electrophoresis Using X-Ray Fluorescence Spectroscopy," Analytical Chemistry, vol. 72, pp. 1754–1758, (2000), incorporated by reference herein. Mann et al. report the preparation of a mixture of chelation complexes of CDTA (cyclohexane diamine tetraacetic acid) and subsequent separation using capillary electrophoresis. The separated complexes were detected using a synchrotron-generated monochromatic, 10 keV x-ray beam.

Many popular drugs include pharmaceutical chemicals that contain the elements fluorine, chlorine, and/or sulfur. X-ray fluorescence spectrometry is especially suited for detecting these types of potential pharmaceutical chemicals because it can be used to detect and quantify these elements, and in general, it can provide information about the quantity of an element with an atomic number of nine or higher. In principle, x-ray fluorescence spectrometry can be used to provide the quantity of any element.

The practice of the invention can be further understood with the accompanying figures. Similar or identical structure is identified using identical callouts. FIG. 1 shows a schematic representation of an embodiment of the apparatus of the invention. Apparatus 10 includes conduit 12, preferably a capillary tube, which is translucent to at least some types of x-rays. Conduit 12 can be made from polyethylene, polypropylene, polytetrafluoroethylene (TEFLON™), polycarbonate, boron nitride, and other materials that are composed of elements having low atomic numbers.

The material and thickness used for conduit 12 can be selected for optimizing the x-ray fluorescence signal and durability of the conduit. The conduit wall should be as thin as practical for maximizing the translucency. Material translucencies for a thickness that attenuates characteristic $K_\alpha$ x-rays of phosphorus, sulfur, chlorine, fluorine, nitrogen, and carbon by a factor of 1/e are listed in Table 1. Preferably, the conduit walls can attenuate the x-ray fluorescence signal by less than a factor of about 10,000. These elements were chosen because they are often present in known pharmaceutical chemicals.

TABLE 1

Thickness in Microns of Material That Attenuates Elemental X-rays by 1/e

| Material | Polyethylene | Teflon | Polycarbonate | Boron nitride | Beryllium |
|---|---|---|---|---|---|
| Phosphorus | 52 | 7 | 28 | 16 | 88 |
| Sulfur | 80 | 11 | 42 | 24 | 136 |
| Chlorine | 120 | 16 | 63 | 37 | 210 |
| Fluorine | 2.1 | 0.4 | 1.2 | 0.7 | 3 |
| Nitrogen | 0.6 | 0.6 | 0.5 | 0.2 | 0.7 |
| Carbon | 0.25 | 0.24 | 0.2 | 0.27 | 0.27 |

Figure 2:
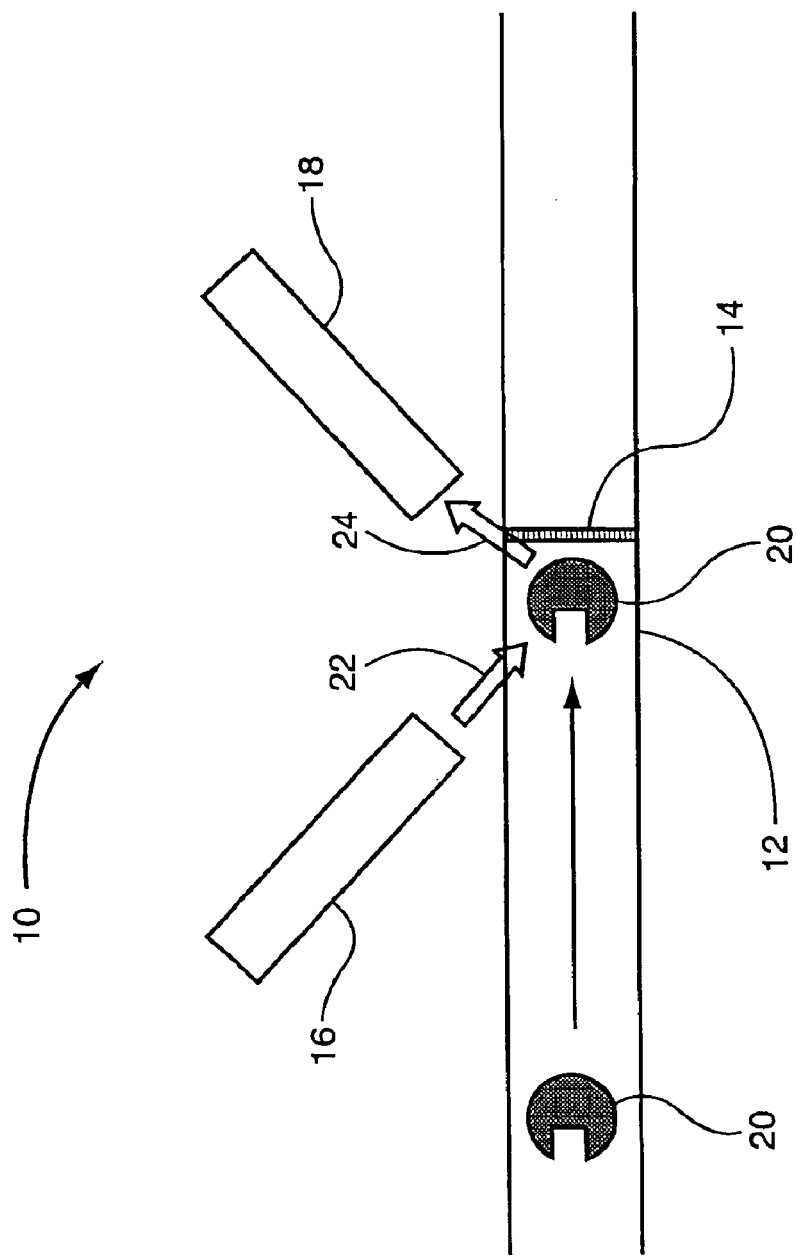
FIG. 2 shows a schematic representation of the apparatus of FIG. 1 as target binder is admitted and collects on the size exclusion filter.
Figure 3:
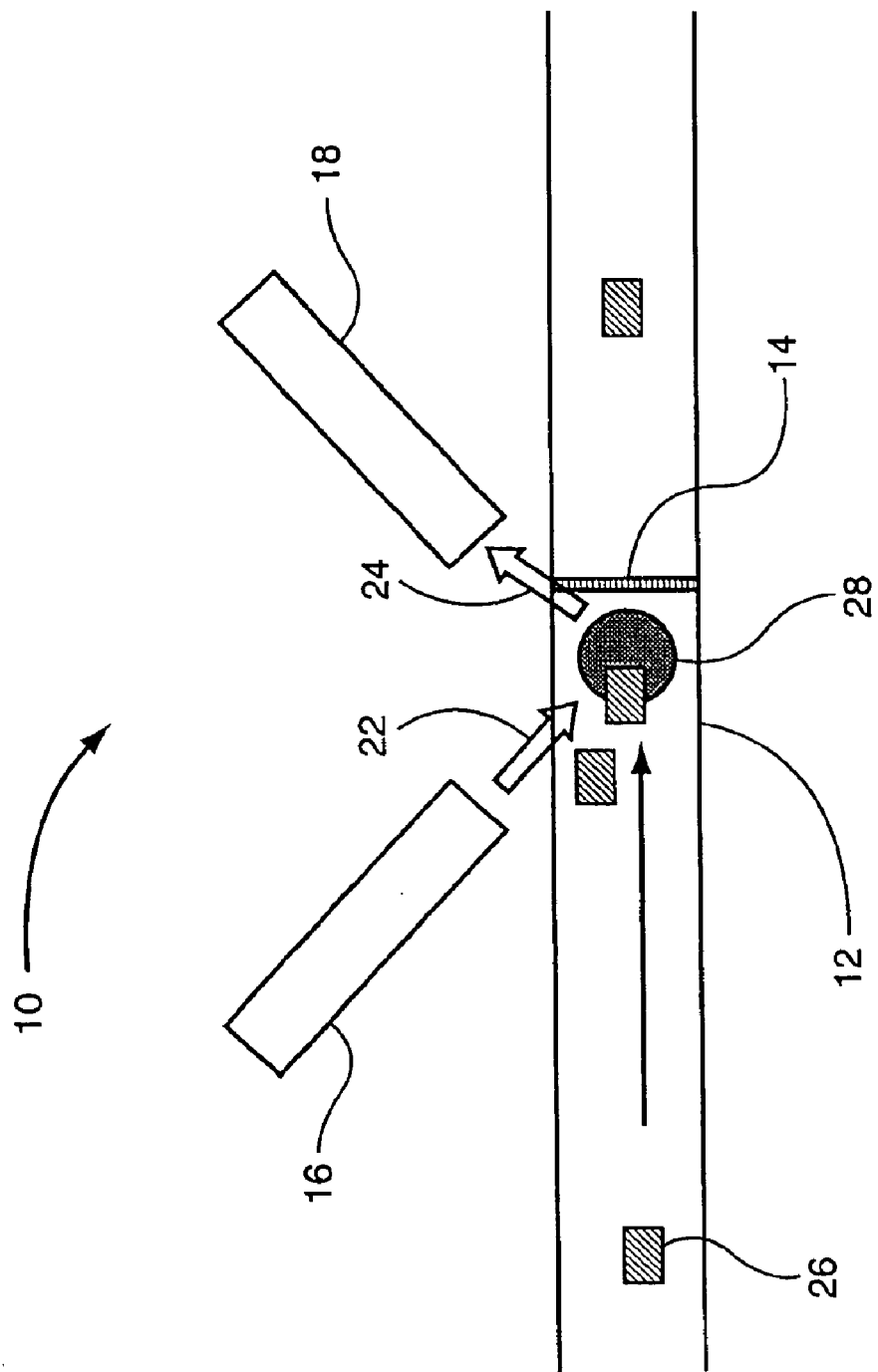
FIG. 3 shows a schematic representation of the apparatus of FIG. 2 after a potential pharmaceutical chemical binds to target binder.

Size exclusion filter 14 remains stationary inside conduit 12. Size exclusion filter 14 includes pores that are small enough to block the flow of the target binders used with the invention but large enough not to block the flow of potential pharmaceutical chemicals being tested for binding to the target binder. For detecting binding between a protein and a potential pharmaceutical chemical, size exclusion filter 14 is preferably a cellulose-based filter (an ULTRACEL™ AMICON™ YM10 Ultrafiltration Disc, for example) or a mesoporous inorganic material such as a zeolite (MCM-41 for example). The key attribute of size exclusion filter 14 is that it blocks the flow of the target binder while not blocking the flow of the potential pharmaceutical chemical being tested. Size exclusion filter 14 can have any shape (e.g. flat, curved, round, etc.) or orientation (e.g. perpendicular as shown in FIGS. 1–3 or at other angles) relative to conduit 12.

Apparatus 10 also includes an x-ray excitation source 16 and an x-ray detector 18. X-ray excitation source 16 sends a beam of x-rays (preferably a collimated and focused beam) to a section of conduit 12. FIG. 1 shows x-ray source pointing at a section near size exclusion filter 14. In practice, x-ray excitation source 16 can be used to obtain a baseline measurement of the concentration of potential pharmaceutical chemical along conduit 12 by sending x-rays to various sections of conduit 12 and detecting the x-ray fluorescence using x-ray detector 18. The wavelength and/or energy of the x-ray fluorescence is used to identify a particular element present in the target binder and/or potential pharmaceutical, and the intensity of the signal is used to for quantification. The x-ray excitation source 16 and x-ray detector 18 used to demonstrate the invention were part of a commercially available spectrometer, the EDAX Eagle II XPL energy dispersive x-ray fluorescence spectrometer, equipped with a microfocus x-ray tube, lithium drifted silicon solid-state detector, processing electronics, and vendor supplied operating software. The x-ray tube provided the source of x-rays, and the lithium drifted silicon detector provided the x-ray fluorescence detector.

While an x-ray tube is the preferred x-ray source of the invention for reasons of cost and ease of use, it should be understood that any excitation source that produces an x-ray fluorescence signal from the target binder, potential pharmaceutical, and complex may be used. In principle, a proton accelerator that is typically used for proton-induced x-ray emission (PIXE) and proton-induced gamma-ray emission (PIGE) may be used with the present invention. PIXE excitation is described by C. Vogt et al. in "Element Sensitive X-ray Detection for Capillary Electrophoresis," J. Chromatography A, vol. 727, pp. 301–310, 1996, incorporated by reference herein.

Any type of x-ray fluorescence detector can be used, such as a wavelength dispersive x-ray fluorescence detector, a total reflection x-ray fluorescence detector, or a confocal x-ray microscope, could be used.

Any target binder may be used with the present invention. Preferable target binders are materials that regulate biological reactions and processes such as glycosylation, phosphorylation, mitosis, meiosis, protein synthesis, endocytosis, cell signaling, respiration, gene expression, cellular adhesion, membrane transport, cellular and cytoskeleton motility, DNA packaging, and the like. Such target binders include, but are not limited to, enzymes, non-enzyme proteins, DNA, RNA, biological cells, and microorganisms (e.g. comprise prions, viruses, bacteria, spores) in whole or in part, and the like. Target binders may also include complexes of enzymes, non-enzyme proteins, DNA, RNA, biological cells, and microorganisms (e.g. comprise prions, viruses, bacteria, spores) in whole or in part, for use in competition studies for example. Preferably, the target binder should not flow through the size exclusion filter but if any amount of target binder does flow through, the flow rate should be much less than that for potential pharmaceutical chemical, preferably by a factor no greater than 1:100 and more preferably by a factor no greater than 1:1000.

Apparatus 10 includes some means for driving fluid through the conduit, preferably a pump (not shown) such as the type of pump typically used for high performance liquid chromatography (HPLC). Other pumps (a peristaltic pump for example) and any other means such as voltage source means typically used for electrophoresis, vacuum source means, and other types of mechanical or electrical means that drive fluids through conduit 12 can be used.

Apparatus 10 may optionally include a collector (not shown) to collect any material that passes through size exclusion filter 14, and analyzers for analyzing these materials. An analyzer (not shown) such as a mass spectrometer, gas chromatograph, liquid chromatograph, or combustion analyzer can be used with the invention. The choice of analyzer will depend on the nature of the chemicals and/or target binders being analyzed. One or more optical absorbance spectrometers (e.g. ultraviolet-visible spectrometry, infrared spectrometry), optical fluorescence spectrometers, and other spectrometers (circular dichroism spectrometer, nuclear magnetic resonance spectrometer, surface plasmon resonance spectrometer) may be used to perform measurements on chemical-target binder complexes, on potential pharmaceutical chemicals, or on target binders present inside the conduit.

FIG. 2 shows apparatus 10 as target binder 20 flows into conduit 12 and FIG. 3 shows apparatus 10 as potential pharmaceutical chemical 26 flows into conduit 12. Some of the potential pharmaceutical chemical 26 flows through filter 14, and some binds to the target binder 20 to form complex 28, which is a complex of the target binder 20 and potential pharmaceutical chemical 26. As x-ray beam 22 is directed at filter 14, the formation of complex 28 is detected as an increase in the intensity of x-ray fluorescence 24 produced by complex 28, which is near filter 14.

The invention may be used for studying the binding affinity between a small molecule (biotin, for example) and a much larger target binder (a protein molecule such as avidin) and the formation and release kinetics of the complex. Avidin is believed to contain from about 10 to about 16 sulfur atoms per avidin molecule, and biotin has one sulfur atom per molecule. In practice, the filter from a CENTRICON™ 30 filter unit, which has a 30,000 Dalton cutoff size, is an acceptable size exclusion filter for blocking the flow of avidin but not the flow of biotin. The x-ray fluorescence detector can be used to quantify the signal due to sulfur as the x-ray source sends x-rays near the filter. The expected increase in signal intensity would indicate that more and more biotin is binding to the avidin. After forming the complex, a solution of buffer could be flowed past the avidin-biotin complex. The expected decrease in the sulfur signal over time could then be used to calculate the release kinetics. The amount of bound biotin can be measured by subtracting the concentration of biotin in the solution from the concentration of biotin measured using x-ray fluorescence near the filter (where the avidin/biotin complex forms). The biotin can be measured by x-ray fluorescence in a section of the conduit far enough upstream of the filter such that the avidin concentration there is minimal. The binding and release kinetics can be determined by comparing the amount of biotin in the complex with the rate of change of the concentration gradient of the biotin in solution.

The invention can also be used in pharmaceutical metabolite studies to detect dangerous metabolic byproducts of a chemical. A blood, cell, tissue, or other biological sample from an animal (a rat, for example) could provide a baseline measurement using the invention. After administering the potential pharmaceutical to the animal, blood would be taken from the animal and examined for the presence of metabolites using the method of the invention.

The invention can also be used in DNA or RNA binding studies. A suitable size exclusion filter that blocked the flow of DNA or RNA through the conduit of the invention would be used. The DNA or RNA could then be quantified using the x-ray fluorescence of its constituent phosphorus atoms. Another molecule of DNA, RNA, protein, or other chemical would then be introduced. After quantifying the amount of this chemical, the binding affinity could then be calculated. Binding kinetics could be determined as described for the biotin/avidin kinetic determination above.

The temperature of the conduit can be controlled. This may be useful, for example, for kinetic and thermodynamic studies of binding, such as determining DNA melting temperatures.

In summary, the present invention provides an apparatus and method for detecting binding events between potential pharmaceutical chemicals and target binders. The present invention uses x-ray fluorescence to determine the presence and relative amounts of elements such as fluorine, chlorine, bromine, iodine, phosphorus, and sulfur, the latter two being important constituents of enzymes, non-enzyme proteins, DNA, and RNA. Thus, the invention provides a non-destructive method of screening the binding of potential pharmaceutical chemical with a target binder such as a protein or a nucleic acid. The invention provides the advantage of not requiring chemicals with tags.

The foregoing description of the invention has been presented for purposes of illustration and description and is not intended to be exhaustive or to limit the invention to the precise form disclosed, and obviously many modifications and variations are possible in light of the above teaching.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A screening method comprising sending a fluid comprising target binder through a conduit to a size exclusion filter, the target binder being too large to pass through the size exclusion filter; sending a second fluid comprising one or more chemicals through the conduit, the one or more chemicals capable of potentially binding to the target binder, the one or more chemicals being small enough to pass through the filter; sending x-rays into the conduit near the size exclusion filter; and monitoring any x-ray fluorescence signal produced from inside the conduit near the size exclusion filter.

2. The screening method of claim 1, further comprising sending x-rays into the conduit upstream of the size exclusion filter and monitoring any x-ray fluorescence signal produced from inside the conduit upstream of the size exclusion filter.

3. The screening method of claim 1, further comprising sending x-rays into the conduit downstream of the size exclusion filter and monitoring any x-ray fluorescence signal produced from inside the conduit downstream of the size exclusion filter.

4. The screening method of claim 1, wherein the fluid comprising target binder and the fluid comprising one or more chemical comprise aqueous solutions.

5. The screening method of claim 1, wherein the target binder participates in a biological process.

6. The screening method of claim 1, wherein the target binder is selected from the group consisting of enzymes, non-enzyme proteins, DNA, RNA, microorganisms, human cells, plant cells, and animal cells.

7. The screening method of claim 1, wherein the chemicals of the solution of one or more chemicals comprise at least one element having an atomic number greater than eight.

* * * * *